United States Patent
Marche et al.

(10) Patent No.: US 12,162,603 B2
(45) Date of Patent: Dec. 10, 2024

(54) SYSTEM AND METHOD TO ENHANCE IN-FLIGHT CONTROLLED REST FOR FLIGHT CREW

(71) Applicant: HONEYWELL INTERNATIONAL INC., Charlotte, NC (US)

(72) Inventors: Stephane Marche, Toulouse (FR); Ratan Khatwa, Redmond, WA (US); Dariia Averkova, Brno (CZ)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 501 days.

(21) Appl. No.: 17/510,620

(22) Filed: Oct. 26, 2021

(65) Prior Publication Data
US 2023/0127393 A1  Apr. 27, 2023

(51) Int. Cl.
*B64D 11/00* (2006.01)
*G06V 20/59* (2022.01)

(52) U.S. Cl.
CPC .............. *B64D 11/00* (2013.01); *G06V 20/59* (2022.01); *B64D 2011/0076* (2013.01)

(58) Field of Classification Search
CPC ....................... B64D 11/00; B64D 2011/0076; B64D 43/00; B64D 45/00; G06V 20/59; A61B 2503/20; A61B 5/4815
See application file for complete search history.

(56) References Cited

U.S. PATENT DOCUMENTS

| | | | | |
|---|---|---|---|---|
| 3,757,100 A | * | 9/1973 | Coleman | G06G 7/78 327/1 |
| 7,027,621 B1 | * | 4/2006 | Prokoski | G06V 40/165 340/576 |

(Continued)

FOREIGN PATENT DOCUMENTS

| | | |
|---|---|---|
| DE | 102020213654 A1 | 5/2022 |
| WO | 2017097940 A1 | 6/2017 |

OTHER PUBLICATIONS

Neuroscience & Biobehavioral Reviews, vol. 44, Jul. 2014, Measuring neurophysiological signals in aircraft pilots and car drivers for the assessment of mental workload, fatigue and drowsiness, Author: Gianluca Borghini a, Laura Astolfi a c, Giovanni Vecchiato a b, Donatella Mattia a, Fabio Babiloni (Year: 2014).*

(Continued)

*Primary Examiner* — Donald J Wallace
*Assistant Examiner* — Jalal C Coduroglu
(74) *Attorney, Agent, or Firm* — Lorenz & Kopf LLP (57) ABSTRACT

In one embodiment, a system to enhance in-flight controlled rest for a flight crew includes a pilot user interface, a co-pilot user interface, and a flight crew monitoring system. The flight crew monitoring system is configured to: (i) determine a physiological state of both a pilot and a co-pilot, (ii) selectively generate one or more alerts for the pilot and/or the co-pilot based on the determined physiological state, (iii) inhibit generating the one or more alerts for the pilot upon receipt of a first inhibit signal from the pilot user interface, (iv) inhibit generating the one or more alerts for the co-pilot upon receipt of a second inhibit signal from the co-pilot user interface, and (v) generate and store data indicating a time of day and a duration that the one or more alerts for the pilot or co-pilot, respectively, were inhibited.

20 Claims, 3 Drawing Sheets

(56) References Cited

U.S. PATENT DOCUMENTS

| | | |
|---|---|---|
| 8,339,285 B2 | 12/2012 | Boren et al. |
| 8,866,623 B2 | 10/2014 | Sharon |
| 9,826,941 B1* | 11/2017 | Serovy .................. A61B 5/747 |
| 10,814,984 B2 | 10/2020 | D'Arbonneau et al. |
| 10,933,982 B2* | 3/2021 | Hubbard ............... B60T 8/1703 |
| 2007/0125909 A1* | 6/2007 | Seiersen ................ B64D 11/00 |
| | | 244/118.5 |
| 2009/0109038 A1 | 4/2009 | Christophe et al. |
| 2009/0125166 A1* | 5/2009 | Johnson ................ B64C 13/507 |
| | | 701/3 |
| 2010/0030406 A1 | 2/2010 | Christophe et al. |
| 2011/0018740 A1* | 1/2011 | Boren ................... B60N 2/976 |
| | | 340/965 |
| 2012/0075119 A1 | 3/2012 | Dorneich et al. |
| 2014/0076318 A1 | 3/2014 | Flower et al. |
| 2016/0318623 A1* | 11/2016 | Zaccaria ............... B64D 45/00 |
| 2017/0096236 A1* | 4/2017 | Nelson ................. B64D 45/00 |
| 2017/0313408 A1* | 11/2017 | Sheffer ................. B64C 13/22 |
| 2018/0225945 A1 | 8/2018 | Moravek et al. |
| 2020/0261017 A1* | 8/2020 | Ruwe ...................... A61B 5/18 |
| 2020/0290740 A1* | 9/2020 | Rangan ................. G08B 21/06 |
| 2021/0034053 A1* | 2/2021 | Nikolic ................. G08G 5/025 |

OTHER PUBLICATIONS

Journal of Safety Research 72 (2020) 173-187 Human Factors and Technology Special Issue Detecting fatigue in car drivers and aircraft pilots by using non-invasive measures: TXinyun Hu†, Gabriel Lodewijks School of Aviation, University of New South Wales, Sydney, Australia (Year: 2020).*

"NBAA Opposes FAA's Opinion On Controlled Crew Rest' for Part 91 Operators," NBAA—National Business Aviation Association, Updated Feb. 6, 2012, downloaded from https://nbaa.org/aircraft-operations/safety/human-factors/fatigue/nbaa-opposes-faas-opinion-on-controlled-crew-rest-for-part-91-operators/, downloaded on Sep. 24, 2021.

Flight Safety Foundation, "Controlled Rest on the Flight Deck: A Resource for Operators," Nov. 2018.

* cited by examiner

SYSTEM AND METHOD TO ENHANCE IN-FLIGHT CONTROLLED REST FOR FLIGHT CREW

TECHNICAL FIELD

The present disclosure generally relates to flight crew in-flight controlled rest, and more particularly relates to systems and methods to enhance in-flight controlled rest for flight crew.

BACKGROUND

For two-person flight crews, some regulatory agencies and airlines allow one person at a time to take a controlled rest. A controlled rest may be, for example, a short sleep duration of less than 40 minutes, and often between 20 and 30 minutes, and is only allowed during the cruise phase of the flight, when flight crew workload is relatively low. During a controlled rest, although the resting flight crew member (pilot or co-pilot) remains in their seat, the on-duty flight crew member must be particularly alert when the other pilot is resting.

After the controlled rest period, the on-duty flight crew member wakes up the resting flight crew member. After waking up, the resting flight crew member does not immediately go back on duty. Rather, due to sleep inertia, they must first wait a 20-minute recovery period. Thereafter, both flight crew members will conduct a post Crew Rest check list. Moreover, in some airlines, the flight attendant is informed of the controlled rest and may check after the rest that both pilots are alert.

The International Civil Aviation Organization (ICAO) has recognized controlled rest as an effective mitigation strategy in response to unanticipated fatigue experienced during flight operations. Hence, there is a need for a system and method that will enhance the controlled rest of flight members. The present disclosure addresses at least this need.

BRIEF SUMMARY

This summary is provided to describe select concepts in a simplified form that are further described in the Detailed Description. This summary is not intended to identify key or essential features of the claimed subject matter, nor is it intended to be used as an aid in determining the scope of the claimed subject matter.

In one embodiment, a system to enhance in-flight controlled rest for a flight crew includes a pilot user interface, a co-pilot user interface, and a flight crew monitoring system. The pilot user interface is configured to receive first user input and, upon receipt of the first user input, to supply a first inhibit signal. The co-pilot user interface is configured to receive second user input and, upon receipt of the user input, to supply a second inhibit signal. The flight crew monitoring system is in operable communication with the pilot user interface and the co-pilot user interface. The flight crew monitoring system is configured to: (i) determine a physiological state of both a pilot and a co-pilot, (ii) selectively generate one or more alerts for the pilot and/or the co-pilot based on the determined physiological state, (iii) inhibit generating the one or more alerts for the pilot upon receipt of the first inhibit signal, (iv) inhibit generating the one or more alerts for the co-pilot upon receipt of the second inhibit signal, and (v) upon receipt of the first inhibit signal or the second inhibit signal, generate and store data indicating a time of day and a duration that the one or more alerts for the pilot or co-pilot, respectively, were inhibited.

In another embodiment, a system to enhance in-flight controlled rest for a flight crew includes a pilot user interface, a co-pilot user interface, and a flight crew monitoring system. The pilot user interface is configured to receive first user input and, upon receipt of the first user input, to supply a first inhibit signal. The co-pilot user interface is configured to receive second user input and, upon receipt of the user input, to supply a second inhibit signal. The flight crew monitoring system is in operable communication with the pilot user interface and the co-pilot user interface. The flight crew monitoring system includes a plurality of pilot sensors configured to supply pilot physiologic and activity data associated with the pilot, a plurality of co-pilot sensors configured to supply co-pilot physiological and activity data associated with the co-pilot, and a processor coupled to receive the pilot physiologic and activity data and the co-pilot physiological and activity data. The processor is configured to: (i) determine a pilot rest quality whenever the first inhibit signal is supplied, (ii) determine a co-pilot rest quality whenever the second inhibit signal is supplied, (iii) determine a pilot fatigue state whenever the first inhibit signal is not supplied, (iv) determine a co-pilot fatigue state whenever the second inhibit signal is not supplied, (v) selectively generate one or more alerts for the pilot and the co-pilot based on the determined pilot fatigue state and the determined co-pilot fatigue state, respectively, (vi) inhibit generating the one or more alerts for the pilot upon receipt of the first inhibit signal, (vii) inhibit generating the one or more alerts for the co-pilot upon receipt of the second inhibit signal, and (viii) upon receipt of the first inhibit signal or the second inhibit signal, generate and store data indicating a time of day and a duration that the one or more alerts for the pilot or co-pilot, respectively, were inhibited.

In yet another embodiment, a method to enhance in-flight controlled rest for a flight crew, includes supplying, in response to first user input to a pilot user interface, a first inhibit signal, and supplying, in response to a second user input to a co-pilot user interface, a second inhibit signal. In a flight crew monitoring system: a physiological state of both a pilot and a co-pilot are determined, one or more alerts for the pilot and/or the co-pilot are selectively generated based on the determined physiological state, the one or more alerts for the pilot are inhibited upon receipt of the first inhibit signal, the one or more alerts for the co-pilot are inhibited upon receipt of the second inhibit signal, and upon receipt of the first inhibit signal or the second inhibit signal, data indicating a time of day and a duration that the one or more alerts for the pilot or co-pilot, respectively, were inhibited are generated and stored.

Furthermore, other desirable features and characteristics of the system and method to enhance in-flight controlled rest for a flight crew will become apparent from the subsequent detailed description and the appended claims, taken in conjunction with the accompanying drawings and the preceding background.

BRIEF DESCRIPTION OF THE DRAWINGS

The present invention will hereinafter be described in conjunction with the following drawing figures, wherein like numerals denote like elements, and wherein.

DETAILED DESCRIPTION

The following detailed description is merely exemplary in nature and is not intended to limit the invention or the application and uses of the invention. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary, or the following detailed description.

Figure 1:
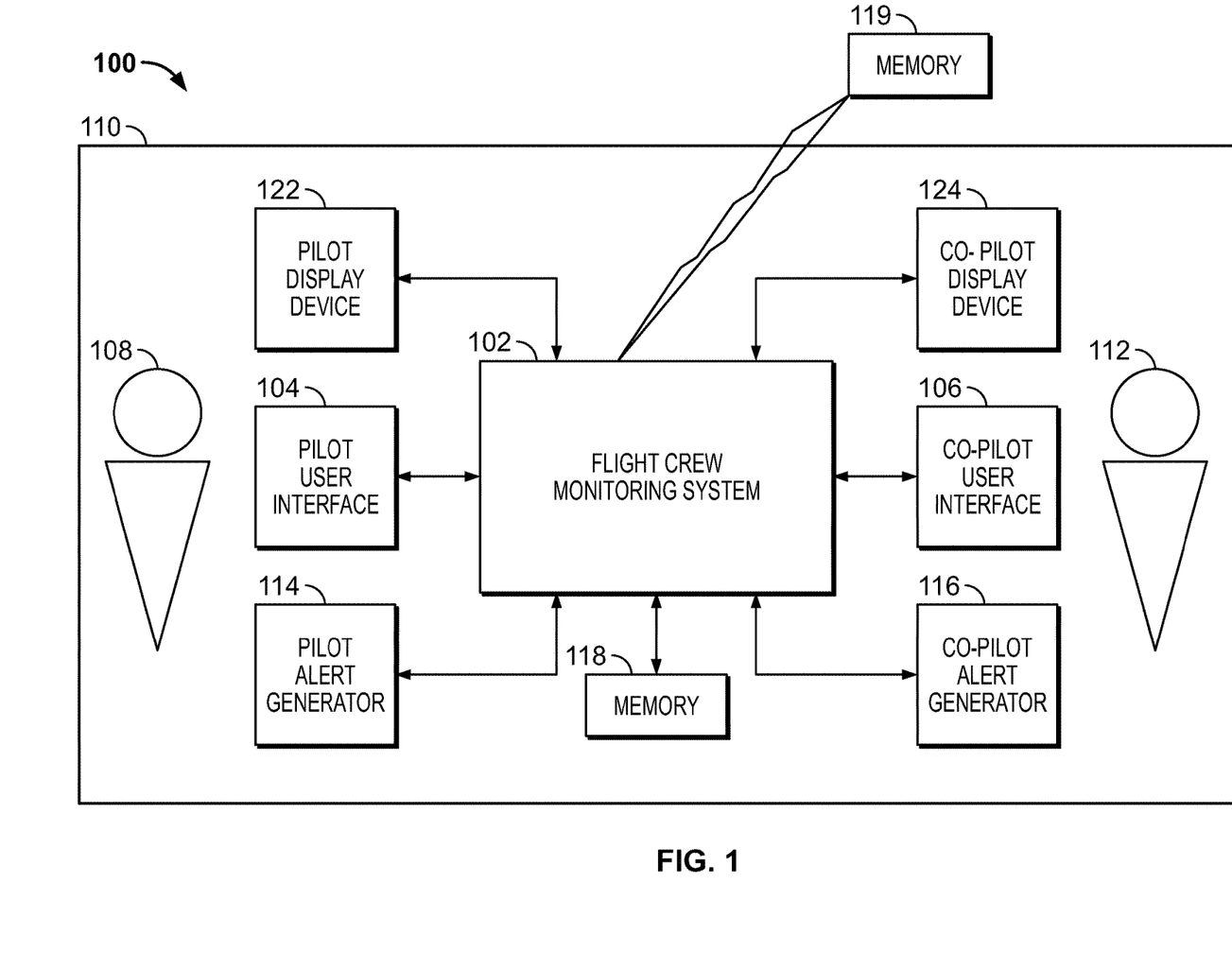
FIG. 1 depicts a functional block diagram of one embodiment of a system to enhance in-flight controlled rest for a flight crew.

Referring to FIG. 1, a functional block diagram of a system to enhance in-flight controlled rest for a flight crew is depicted and includes a flight crew monitoring system 102, a pilot user interface 104, and a co-pilot user interface 106, all of which are preferably disposed within an aircraft 110. The flight crew monitoring system 102 is in operable communication with the pilot user interface 104 and the co-pilot user interface 106 and is configured to determine the physiological state of both a pilot 108 and a co-pilot 112, and to selectively generate one or more alerts for the pilot 108 and/or the co-pilot 112 based on the determined physiological state. To do so, and as shown more clearly in FIG. 2, the flight crew monitoring system 102, at least in the depicted embodiment, includes one or more pilot sensors 202, one or more co-pilot sensors 204, and a processor 206. The one or more pilot sensors 202 are configured to supply pilot physiologic and activity data associated with the pilot 108, and the one or more co-pilot sensors 204 are configured to supply co-pilot physiological and activity data associated with the co-pilot 112.

Figure 2:
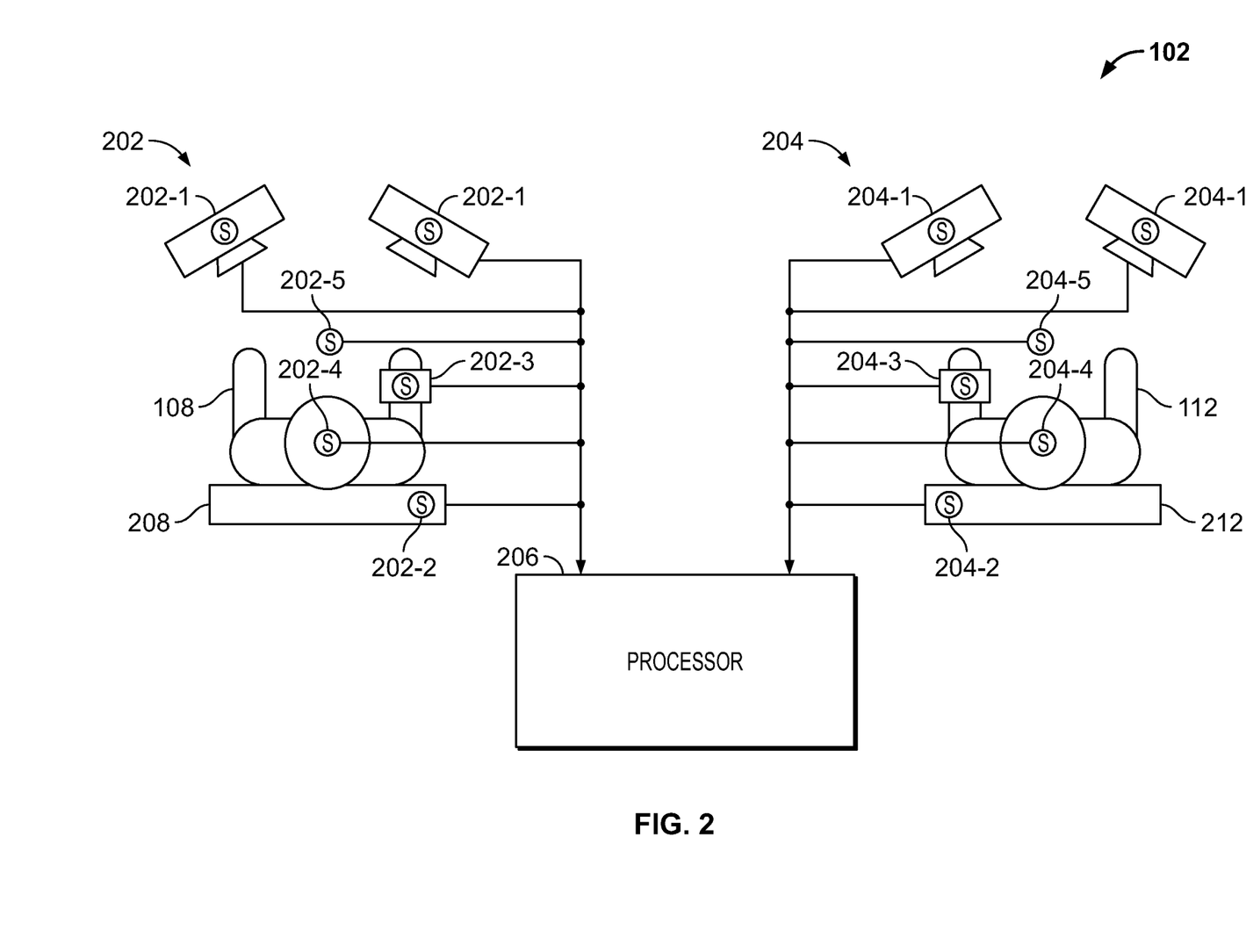
FIG. 2 depicts a functional block diagram of one embodiment of a flight crew monitoring system that may be used to implement the system of FIG. 1.

The one or more pilot sensors 202 (e.g., 202-1, 202-2, 202-3, . . . 202-N) are disposed on, or at least adjacent to, the pilot 108, and the one or more co-pilot sensors 204 (e.g., 204-1, 204-2, 204-3, . . . 204-N) are disposed on, or at least adjacent to, the co-pilot 112. It will be appreciated that the number and type of pilot sensors 202 and co-pilot sensors 204 may vary. For example, the one or more pilot sensors 202 and the one or more co-pilot sensors 204 may each include at least one or more video sensors 202-1, 204-1. In some embodiments the one or more pilot sensors 202 and the one or more co-pilot sensors 204 may additionally include one or more seat load sensors 202-2, 204-2, one or more electrocardiogram (ECG) sensors 202-3, 204-3, one or more electroencephalogram (EEG) sensors 202-4, 204-4, one or more electrooculogram (EOG) sensors 202-5, 204-5, and/or one or more inertial sensors 202-6, 204-6. In some embodiments, the pilot sensors 202 and co-pilot sensors 204 may also include electro-dermal sensors, eye tracking sensors, and breathing sensors, just to name a few non-limiting examples.

The one or more video sensors 202-1, 204-1 when included, are disposed adjacent to the pilot 108 and co-pilot 112 and detect, for example, various facial features and bodily movements of the pilot 108 and co-pilot 112. These facial features may vary, but include, for example, one or more of eyelid movements, eye movements, gaze direction, mouth morphology, and facial expressions, just to name a few. The one or more seat load sensors 202-2, 204-2, when included, are disposed within the pilot seat and the co-pilot seat and detect, for example, the posture state and in-seat movements of the pilot 108 and co-pilot 112. The one or more ECG sensors 202-3, 204-3, when included, are disposed on the pilot 108 and co-pilot 112 and detect the heart rate of the on-duty operator 102. The one or more EEG sensors 202-4, 204-4 sensors, when included, are disposed on the pilot 108 and co-pilot 112 and detect, for example, the brain wave activity of the pilot's 108 and co-pilot's 112 brain. The one or more EOG sensors 202-5, 204-5, when included, are also disposed on the pilot 108 and co-pilot 112 and detect, for example, eye movements of the pilot 108 and co-pilot 112. The one or more inertial sensors 202-6, 204-6, when included, are disposed on the pilot 108 and co-pilot 112 and detect, for example, bodily movements of the pilot 108 and co-pilot 112.

It is known that various facial features, body and facial movements, posture, in-seat activity, and heart rate can all be correlated to, and used to provide a measure of, the fatigue state of a person, such as the pilot 108 or co-pilot 112. It is additionally known that brain wave activity, eye movement, and bodily movement can all be used to measure a person's sleep duration, sleep phase, and time in (or since) a particular sleep phase. These factors, as is also known, can be correlated to, and used to provide a measure of, the rest quality of a person, such as the pilot 108 or co-pilot 112.

The processor 206 generally represents the hardware, circuitry, processing logic, and/or other components configured to facilitate communications and/or interaction between the elements of the flight crew monitoring system 102 and perform additional processes, tasks and/or functions to support operation of the flight crew monitoring system 102, as described in greater detail below. Depending on the embodiment, the processor 206 may be implemented or realized with a general purpose processor, a controller, a microprocessor, a microcontroller, a content addressable memory, a digital signal processor, an application specific integrated circuit, a field programmable gate array, any suitable programmable logic device, discrete gate or transistor logic, processing core, discrete hardware components, or any combination thereof, designed to perform the functions described herein. In practice, the processor 206 includes processing logic that may be configured to carry out the functions, techniques, and processing tasks associated with the operation of the flight crew monitoring system 102 described in greater detail below. Furthermore, the steps of a method or algorithm described in connection with the embodiments disclosed herein may be embodied directly in hardware, in firmware, in a software module executed by the processor 206, or in any practical combination thereof. In accordance with one or more embodiments, the processor 206 includes or otherwise accesses a data storage element, such as a memory (e.g., RAM memory, ROM memory, flash memory, registers, a hard disk, or the like) or another suitable non-transitory short or long term storage media capable of storing computer-executable programming instructions or other data for execution that, when read and executed by the processor 206, cause the processor 206 to execute and perform one or more of the processes, tasks, operations, and/or functions described herein.

The processor 206 is in operable communication, using any one of numerous wired or wireless techniques, with the pilot sensors 202 and the co-pilot sensors 204. The processor 206 receives the pilot physiologic and activity data and the co-pilot physiological data and is configured to selectively determine, using known techniques and algorithms, pilot fatigue state, co-pilot fatigue state, pilot rest quality, and co-pilot rest quality. In particular, and with reference back to FIG. 1, it was noted that the flight crew monitoring system 102 is configured to selectively generate one or more alerts for the pilot and/or the co-pilot based on the determined physiological state. More specifically, the flight crew monitoring system 102 will generate one or more alerts for the pilot 108 when, for example, the pilot fatigue state exceeds a predetermined fatigue state threshold and generate one or more alerts for the co-pilot 112 when, for example, the co-pilot fatigue state exceeds the predetermined fatigue state threshold.

The alerts may be provided via a pilot alert generator 114 and a co-pilot alert generator 116. The pilot alert generator 114 and the co-pilot alert generator 116 are each configured, upon receipt of an appropriate alert signal, to generate an alert indicating that the fatigue state of the pilot 108 or the fatigue state of the co-pilot 112, respectively, exceeds a predetermined fatigue state threshold. It will be appreciated that the alert generators 114, 116 may be implemented using any one of more types of known alert generating devices and may thus generate the alert using any one or more known techniques. For example, the alert generator may be configured to generate one or more of an audible alert, a visual alert, and/or a haptic alert.

Whenever the pilot 108 or the co-pilot 112 decide to take a controlled rest, it is desirable that the flight crew monitoring system 102 not generate the one or more alerts for the resting pilot 108 or co-pilot 112, respectively, to avoid waking or disturbing the resting pilot 108 or co-pilot 112. This is where the pilot and co-pilot user interfaces 104, 106 come into play. It will be appreciated that the pilot and co-pilot user interfaces 104, 106 may be implemented using any one of numerous user interface devices. Some non-limiting examples include a simple push-button interface, a touchscreen interface, a graphical user interface (GUI), a voice-controlled interface, just to name a few, which may be implemented, in some embodiments, on a wearable device, such as a smart watch, or headset, just to name a few. In still other embodiments, the pilot and co-pilot user interfaces 104, 106 could be implemented as part of the pilot seat 208 and co-pilot seat 212, respectively, or as part of eye masks or hoods that are used during a rest period.

Regardless of how the pilot and co-pilot user interfaces 104, 106 are specifically implemented, each is configured to receive user input and supply signals in response to the received user input. In particular, the pilot user interface 104 is configured to receive first user input and, upon receipt of the first user input, to supply a first inhibit signal to the flight crew monitoring system 102, and the co-pilot user interface 106 is configured to receive second user input and, upon receipt of the second user input, to supply a second inhibit signal to the flight crew monitoring system 102. In those embodiments in which the pilot and co-pilot user interfaces 104, 106 are implemented as part of the pilot and co-pilot seats 208, 212, respectively, the first and second user inputs are supplied indirectly, via movement of the pilot and co-pilot seats 208, 212, respectively, to a predetermined position. In those embodiments in which the pilot and co-pilot user interfaces 104, 106 are implemented as part of eye masks or hoods, the inhibit signals are generated upon the masks or hoods being donned.

In addition to the functions described above, the flight crew monitoring system 102 is further configured to selectively inhibit generating the one or more alerts for the pilot 108 or the co-pilot 112. More specifically, the flight crew monitoring system 102 is configured to inhibit generating the one or more alerts for the pilot 108 upon receipt of the first inhibit signal, and to inhibit generating the one or more alerts for the co-pilot 112 upon receipt of the second inhibit signal. The flight crew monitoring system 102 is additionally configured, upon receipt of the first inhibit signal or the second inhibit signal, to generate and store, in memory 118, data that indicates the time of day and the duration that the one or more alerts for the pilot or co-pilot, respectively, were inhibited. This data may be used generate a report as to when and how long the associated alerts were inhibited.

After the resting flight crew member (pilot 108 or co-pilot 112) has completed their rest period, the one or more alerts for that flight crew member will need to once again be enabled. This enablement may occur automatically or in response to user input. If the flight crew monitoring system 102 is configured to automatically re-enable the one or more alerts, then, as may be appreciated, it is configured, upon receipt of the first inhibit signal or the second inhibit signal, to inhibit generating the one or more alerts for the pilot or the one or more alerts for the co-pilot, respectively, for a predetermined time period and to automatically enable generating the one or more alerts for the pilot or the one or more alerts for the co-pilot, respectively, after the predetermined time period expires. The predetermined time period may be a fixed time period that is not adjustable by the pilot 108 or co-pilot 112, or it may be a variable time period that is adjustable.

If the flight crew monitoring system 102 is configured to re-enable the one or more alerts in response to user input, the user input will preferably be supplied to the pilot user interface 104 or the co-pilot user interface 106. That is, for such embodiments, the pilot user interface 104 is further configured to receive third user input and, upon receipt of the third user input, to supply a first enable signal, and the co-pilot user interface 106 is configured to receive fourth user input and, upon receipt of the fourth user input, to supply a second enable signal. Moreover, the flight crew monitoring system 102 is configured to enable generating the one or more alerts for the pilot 108 upon receipt of the first enable signal, and to enable generating the one or more alerts for the co-pilot 112 upon receipt of the second enable signal. In those embodiments in which the pilot and co-pilot user interfaces 104, 106 are implemented as part of the pilot and co-pilot seats 208, 212, respectively, the third and fourth user inputs are again supplied indirectly, via movement of the pilot and co-pilot seats 208, 212, respectively, to a predetermined position. In those embodiments in which the pilot and co-pilot user interfaces 104, 106 are implemented as part of eye masks or hoods, the enable signals are generated upon the masks or hoods being removed.

As was previously noted, flight crew monitoring system 102, and more specifically the processor 206, is configured to determine pilot fatigue state, co-pilot fatigue state, pilot rest quality, and co-pilot rest quality. As may appreciated, the processor 206 is configured to determine the pilot fatigue state whenever the first inhibit signal is not supplied, determine the co-pilot fatigue state whenever the second inhibit signal is not supplied, determine pilot rest quality whenever the first inhibit signal is supplied, and determine co-pilot rest quality whenever the second inhibit signal is supplied.

In some embodiments, the flight crew monitoring system 102 is not only configured to determine pilot and co-pilot rest quality, it is further configured to generate pilot rest quality data, which is indicative of the determined pilot rest quality, and co-pilot rest quality data, which is indicative of the determined co-pilot rest quality. These data may then be transmitted to memory 118, or it may additionally or instead be transmitted to a memory 119 that is disposed remote from the flight crew monitoring system 102.

It may also be useful to provide the pilot and co-pilot with a visual display of their rest quality. Thus, as FIG. 1 also depicts, in some embodiments the system 100 may additionally include one or more display devices. In the depicted embodiment, the system includes a pilot display device 122 and a co-pilot display device 124, both of which are in operable communication with the flight crew monitoring system 102. When these display devices 122, 124 are included, the flight crew monitoring system 102 is further configured to command the display devices 122, 124 to render one or more images representative of the determined rest quality of the pilot or the co-pilot, respectively.

Figure 3:
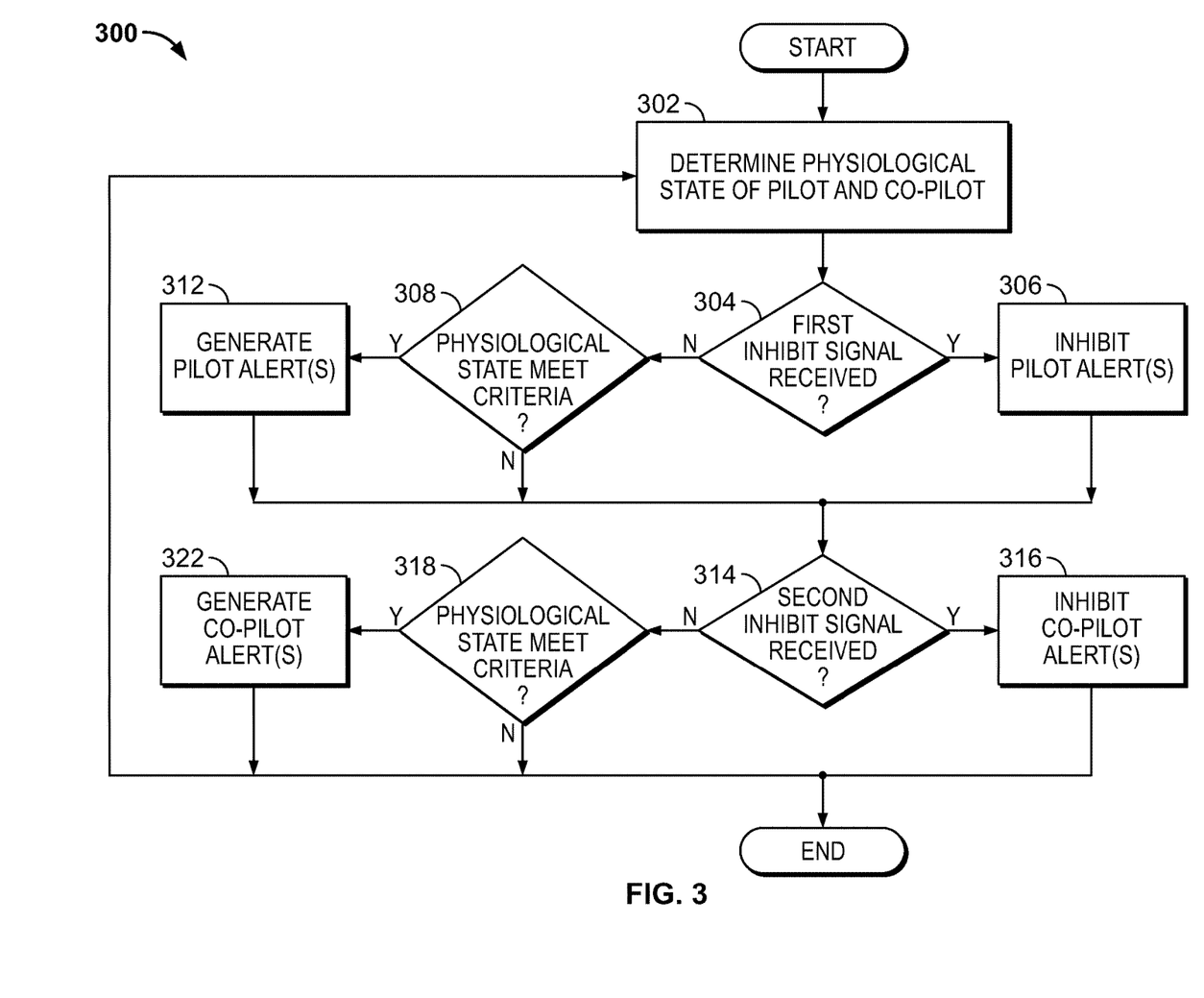
FIG. 3 general process, which may be implemented in the system 100 of FIG. 1.

Referring now to FIG. 3, the general process, which may be implemented in the system 100 of FIG. 1, is depicted in flowchart form and will now be described. The process 300 includes determining the physiological state of both the pilot 108 and the co-pilot 112 (302). The process 300 further includes determining if the first inhibit signal has been supplied (304). If it has, then the alerts for the pilot are inhibited (306). If it has not, then a determination is made as to whether the physiological state of the pilot 108 has met one or more predetermined criteria (308). If it has, then an alert for the pilot is generated (312) and the process moves to determining if the second inhibit signal has been supplied (314). If the physiological state of the pilot 108 has not met the one or more predetermined criteria, the process moves directly to determining if the second inhibit signal has been supplied (314).

If the second inhibit signal has been supplied, then the alerts for the co-pilot are inhibited (316). If it has not, then a determination is made as to whether the physiological state of the co-pilot 112 has met the one or more predetermined criteria (318). If it has, then an alert for the co-pilot is generated (322) and the process returns to determining the physiological state of both the pilot 108 and the co-pilot 112 (302). If the physiological state of the co-pilot 112 has not met the one or more predetermined criteria, the process moves directly to determining the physiological state of both the pilot 108 and the co-pilot 112 (302).

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations.

The various illustrative logical blocks, modules, and circuits described in connection with the embodiments disclosed herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. In practice, one or more processor devices can carry out the described operations, tasks, and functions by manipulating electrical signals representing data bits at memory locations in the system memory, as well as other processing of signals. The memory locations where data bits are maintained are physical locations that have particular electrical, magnetic, optical, or organic properties corresponding to the data bits. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or instructions that perform the various tasks. The program or code segments can be stored in a processor-readable medium or transmitted by a computer data signal embodied in a carrier wave over a transmission medium or communication path. The "computer-readable medium", "processor-readable medium", or "machine-readable medium" may include any medium that can store or transfer information. Examples of the processor-readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, or the like. The computer data signal may include any signal that can propagate over a transmission medium such as electronic network channels, optical fibers, air, electromagnetic paths, or RF links. The code segments may be downloaded via computer networks such as the Internet, an intranet, a LAN, or the like.

Some of the functional units described in this specification have been referred to as "modules" in order to more particularly emphasize their implementation independence. For example, functionality referred to herein as a module may be implemented wholly, or partially, as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices, or the like. Modules may also be implemented in software for execution by various types of processors. An identified module of executable code may, for instance, comprise one or more physical or logical modules of computer instructions that may, for instance, be organized as an object, procedure, or function. Nevertheless, the executables of an identified module need not be physically located together, but may comprise disparate instructions stored in different locations that, when joined logically together, comprise the module and achieve the stated purpose for the module. Indeed, a module of executable code may be a single instruction, or many instructions, and may even be distributed over several different code segments, among different programs, and across several memory devices. Similarly, operational data may be embodied in any suitable form and organized within any suitable type of data structure. The operational data may be collected as a single data set, or may be distributed over different locations including over different storage devices, and may exist, at least partially, merely as electronic signals on a system or network.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominantly in the respective nominal axial or radial direction. As used herein, the term "substantially" denotes within 5% to account for manufacturing tolerances. Also, as used herein, the term "about" denotes within 5% to account for manufacturing tolerances.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A system to enhance in-flight controlled rest for a flight crew, comprising:
   a pilot user interface configured to receive first user input and, upon receipt of the first user input, to supply a first inhibit signal;
   a co-pilot user interface configured to receive second user input and, upon receipt of the user input, to supply a second inhibit signal; and
   a flight crew monitoring system in operable communication with the pilot user interface and the co-pilot user interface, the flight crew monitoring system configured to:
   (i) determine a physiological state of both a pilot and a co-pilot,
   (ii) selectively generate one or more alerts for the pilot and/or the co-pilot based on the determined physiological state,
   (iii) inhibit generating the one or more alerts for the pilot upon receipt of the first inhibit signal,
   (iv) inhibit generating the one or more alerts for the co-pilot upon receipt of the second inhibit signal, and
   (v) upon receipt of the first inhibit signal or the second inhibit signal, generate and store data indicating a time of day and a duration that the one or more alerts for the pilot or co-pilot, respectively, were inhibited.

2. The system of claim 1, wherein the flight crew monitoring system is further configured, upon receipt of the first inhibit signal or the second inhibit signal, to inhibit generating the one or more alerts for the pilot or the one or more alerts for the co-pilot, respectively, for a predetermined time period.

3. The system of claim 1, wherein the flight crew monitoring system is further configured to automatically enable generating the one or more alerts for the pilot or the one or more alerts for the co-pilot, respectively, after the predetermined time period expires.

4. The system of claim 1, wherein the flight crew monitoring system comprises:
one or more pilot sensors configured to supply pilot physiologic and activity data associated with the pilot;
one or more co-pilot sensors configured to supply co-pilot physiological and activity data associated with the co-pilot; and
a processor coupled to receive the pilot physiologic and activity data and the co-pilot physiological and activity data and configured to determine:
(i) a pilot rest quality whenever the first inhibit signal is supplied, and
(ii) a co-pilot rest quality whenever the second inhibit signal is supplied.

5. The system of claim 4, wherein the processor is further configured to determine:
(i) a pilot fatigue state whenever the first inhibit signal is not supplied, and
(ii) a co-pilot fatigue state whenever the second inhibit signal is not supplied.

6. The system of claim 5, further comprising:
a pilot display device in operable communication with the flight crew monitoring system; and
a co-pilot display device in operable communication with the flight crew monitoring system,
wherein the flight crew monitoring system is further configured to command the pilot display device or the co-pilot display device to render one or more images representative of the determined pilot rest quality or the determined the co-pilot rest quality, respectively.

7. The system of claim 4, wherein the processor is further configured to generate pilot rest quality data and co-pilot rest quality data, the pilot rest quality data and the co-pilot rest quality data indicative of the determined rest quality of the pilot or the co-pilot, respectively.

8. The system of claim 7, further comprising:
memory in operable communication with the flight crew monitoring system, the memory configured to receive and store the pilot rest quality data and the co-pilot rest quality data.

9. The system of claim 8, wherein the flight crew monitoring system is further configured to at least selectively transmit the pilot rest quality data and the co-pilot rest quality data to the memory.

10. The system of claim 9, wherein:
the flight crew monitoring system is disposed inside an aircraft; and
the memory is located outside of the aircraft.

11. The system of claim 1, wherein:
the pilot user interface is further configured to receive third user input and, upon receipt of the third user input, to supply a first enable signal;
a co-pilot user interface configured to receive fourth user input and, upon receipt of the fourth user input, to supply a second enable signal;
the flight crew monitoring system configured to:
enable generating the one or more alerts for the pilot upon receipt of the first enable signal, and
enable generating the one or more alerts for the co-pilot upon receipt of the second enable signal.

12. A system to enhance in-flight controlled rest for a flight crew, comprising:
a pilot user interface configured to receive first user input and, upon receipt of the first user input, to supply a first inhibit signal;
a co-pilot user interface configured to receive second user input and, upon receipt of the user input, to supply a second inhibit signal; and
a flight crew monitoring system in operable communication with the pilot user interface and the co-pilot user interface, the flight crew monitoring system comprising:
one or more pilot sensors configured to supply pilot physiologic and activity data associated with the pilot;
one or more co-pilot sensors configured to supply co-pilot physiological and activity data associated with the co-pilot; and
a processor coupled to receive the pilot physiologic and activity data and the co-pilot physiological and activity data and configured to:
(i) determine a pilot rest quality whenever the first inhibit signal is supplied,
(ii) determine a co-pilot rest quality whenever the second inhibit signal is supplied,
(iii) determine a pilot fatigue state whenever the first inhibit signal is not supplied,
(iv) determine a co-pilot fatigue state whenever the second inhibit signal is not supplied
(v) selectively generate one or more alerts for the pilot and the co-pilot based on the determined pilot fatigue state and the determined co-pilot fatigue state, respectively,
(vi) inhibit generating the one or more alerts for the pilot upon receipt of the first inhibit signal,
(vii) inhibit generating the one or more alerts for the co-pilot upon receipt of the second inhibit signal, and
(viii) upon receipt of the first inhibit signal or the second inhibit signal, generate and store data indicating a time of day and a duration that the one or more alerts for the pilot or co-pilot, respectively, were inhibited.

13. The system of claim 12, wherein the processor is further configured, upon receipt of the first inhibit signal or the second inhibit signal, to inhibit generating the one or more alerts for the pilot or the one or more alerts for the co-pilot, respectively, for a predetermined time period.

14. The system of claim 12, wherein the processor is further configured to automatically enable generating the one or more alerts for the pilot or the one or more alerts for the co-pilot, respectively, after the predetermined time period expires.

15. The system of claim 12, wherein the processor is further configured to generate pilot rest quality data and co-pilot rest quality data, the pilot rest quality data and the co-pilot rest quality data indicative of the determined rest quality of the pilot or the co-pilot, respectively.

16. The system of claim 15, further comprising:
a pilot display device in operable communication with the flight crew monitoring system; and
a co-pilot display device in operable communication with the flight crew monitoring system, wherein the flight crew monitoring system is further configured to command the pilot display device or the co-pilot display device to render one or more images representative of the determined pilot rest quality or the determined co-pilot rest quality, respectively.

17. The system of claim 12, further comprising:
memory in operable communication with the flight crew monitoring system, the memory configured to receive and store the pilot rest quality data and the co-pilot rest quality data,
wherein the flight crew monitoring system is further configured to at least selectively transmit the pilot rest quality data and the co-pilot rest quality data to the memory.

18. The system of claim 17, wherein:
the flight crew monitoring system is disposed inside an aircraft; and
the memory is located outside of the aircraft.

19. The system of claim 12, wherein:
the pilot user interface is further configured to receive third user input and, upon receipt of the third user input, to supply a first enable signal;
a co-pilot user interface configured to receive fourth user input and, upon receipt of the fourth user input, to supply a second enable signal;
the flight crew monitoring system configured to:
enable generating the one or more alerts for the pilot upon receipt of the first enable signal, and
enable generating the one or more alerts for the co-pilot upon receipt of the second enable signal.

20. A method to enhance in-flight controlled rest for a flight crew, comprising the steps of:
supplying, in response to first user input to a pilot user interface, a first inhibit signal;
supplying, in response to a second user input to a co-pilot user interface, a second inhibit signal; and
in a flight crew monitoring system:
determining a physiological state of both a pilot and a co-pilot;
selectively generating one or more alerts for the pilot and/or the co-pilot based on the determined physiological state;
inhibiting the one or more alerts for the pilot upon receipt of the first inhibit signal;
inhibiting the one or more alerts for the co-pilot upon receipt of the second inhibit signal; and
upon receipt of the first inhibit signal or the second inhibit signal, generating and storing data indicating a time of day and a duration that the one or more alerts for the pilot or co-pilot, respectively, were inhibited.

* * * * *